United States Patent [19]
Hellmuth

[11] Patent Number: 5,975,699
[45] Date of Patent: Nov. 2, 1999

[54] METHOD AND APPARATUS FOR SIMULTANEOUSLY MEASURING THE LENGTH AND REFRACTIVE ERROR OF AN EYE

[75] Inventor: Thomas Hellmuth, Aalen, Germany

[73] Assignee: Carl Zeiss, Inc., Thornwood, N.Y.

[21] Appl. No.: 09/069,644

[22] Filed: Apr. 29, 1998

[51] Int. Cl.⁶ .................................................. A61B 3/10
[52] U.S. Cl. ........................................ 351/211; 351/221
[58] Field of Search .................................. 351/205, 211, 351/212, 221; 606/5, 4, 3; 356/359

[56] References Cited

U.S. PATENT DOCUMENTS

| | | | |
|---|---|---|---|
| 3,822,932 | 7/1974 | Humphrey | 351/17 |
| 4,541,697 | 9/1985 | Remijan | 351/211 |
| 4,650,301 | 3/1987 | Humphrey | 351/211 |
| 5,490,849 | 2/1996 | Smith | 606/5 |

OTHER PUBLICATIONS

Optical Coherence Tomography by A. F. Fercher, J. Biomedical Optics, vol. 1, No. 2, pp. 157–173, Apr., 1996.
"Sensors in Ophthalmology" by T. Hellmuth, at pp. 290–323 in a book entitled "Sensors Update," ed. by H. Baltes, W. Göpel, and J. Hesse, Published by Wiley–VCH Verlag GmbH, Weinheim, Germany in 1998.

*Primary Examiner*—George Manuel
*Attorney, Agent, or Firm*—Michael B. Einschlag

[57] ABSTRACT

Embodiments of the present invention are method and apparatus for simultaneously measuring the length and refractive error of an eye, preferably in a non-contact mode. In particular, an embodiment of the present invention is an apparatus which measures length and refractive error of an eye which includes: (a) a source of short coherence radiation which couples radiation into a Michelson interferometer, the arms of the Michelson interferometer having a predetermined optical pathlength difference; (b) an injector which couples radiation output from the interferometer into the eye; and (c) a relay system which couples radiation output from the eye to a spectrometer; wherein the spectrometer measures displacement of radiation to measure the refractive error and the spectrometer measures density of fringes to measure the length.

12 Claims, 1 Drawing Sheet

METHOD AND APPARATUS FOR SIMULTANEOUSLY MEASURING THE LENGTH AND REFRACTIVE ERROR OF AN EYE

TECHNICAL FIELD OF THE INVENTION

The present invention relates to method and apparatus for simultaneously measuring the length and refractive error of an eye in a non-contact mode.

BACKGROUND OF THE INVENTION

Intraocular lenses are used to replace a lens in a patient's eye in the case of cataracts. In such instances, it is important to measure the length and refractive error of the patient's eye in order to provide an appropriate replacement for the lens. In many of these cases, however, it is not possible to use standard optical refractometry because the fundus is not visible through the turbid cataract eye lens. Standard optical refractometry suffers from the additional drawback that it does not measure the length of the patient's eye.

Ultrasound biometry is a method that is used to measure the length of the patient's eye. In performing ultrasound biometry, an ultrasound transducer is placed on the cornea of the patient's eye. Next, an ultrasound pulse is emitted by the transducer and is reflected back from the fundus of the eye. As is well known, the time of flight of the pulse depends on the length of, and the index of refraction of the ultrasound pulse in, the patient's eye. Using this information, the length of the patient's eye can be determined. However, there is a drawback in using ultrasound biometry. In particular, in order to receive an echo which is strong enough to be measured with a suitable signal-to-noise ratio, the ultrasound transducer has to be brought into contact with the patient's eye and a special contact jelly has to be used. This is a problem in that the method is invasive and, in many countries, only a medical doctor is permitted to use this method.

An alternative method used to measure the length of the patient's eye makes use of short coherence interferometry and is free from the above-described drawback. This alternative method is described in an article entitled "Optical Coherence Tomography" by A. Fercher, *Journal of Biomedical Optics*, Vol. 1, No.2, April, 1996, pp. 157–173 (the "Fercher article"). However, this alternative method is limited in that it only measures the length, and not the refractive error, of the patient's eye.

In light of the above, there is a need for a method and apparatus for simultaneously measuring the length and refractive error of an eye, preferably in a non-contact mode.

SUMMARY OF THE INVENTION

Advantageously, embodiments of the present invention are method and apparatus for simultaneously measuring the length and refractive error of an eye in a non-contact mode. In particular, an embodiment of the present invention is an apparatus which measures length and refractive error of an eye which comprises: (a) a source of short coherence radiation which couples radiation into a Michelson interferometer, the arms of the Michelson interferometer having a predetermined optical pathlength difference; (b) an injector which couples radiation output from the interferometer into the eye; and (c) a relay system which couples radiation output from the eye to a spectrometer; wherein the spectrometer measures displacement of radiation to measure the refractive error and the spectrometer measures density of fringes to measure the length.

DETAILED DESCRIPTION

Figure 1:
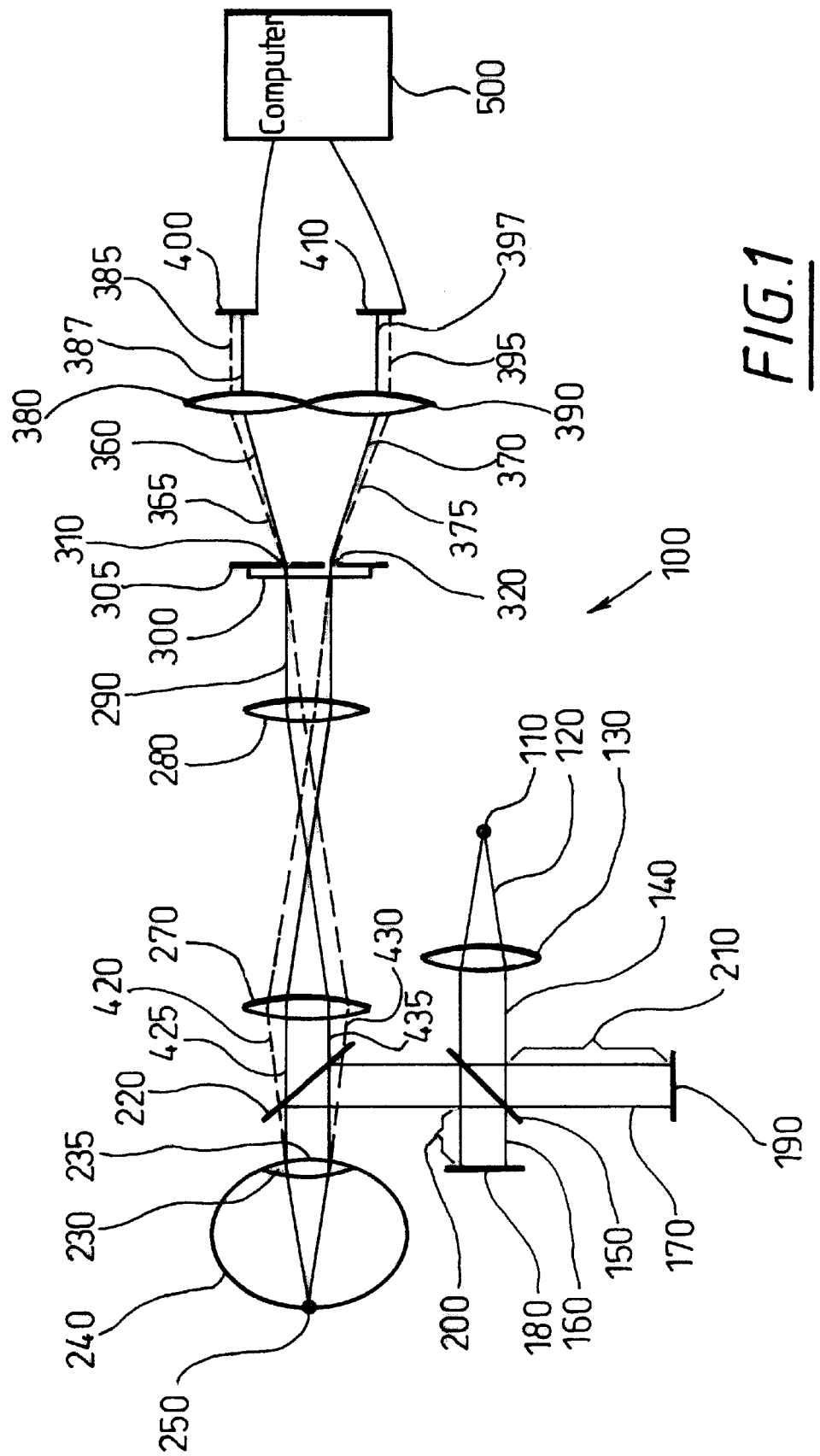
FIG. 1 shows, in pictorial form, an embodiment of the present invention that is used for simultaneously measuring the length and refractive error of an eye in a non-contact mode.

FIG. 1 shows, in pictorial form, embodiment 100 of the present invention that is used for simultaneously measuring the length and refractive error of an eye in a non-contact mode. As shown in FIG. 1, embodiment 100 of the present invention is comprised of a short coherence light source 110. In the preferred embodiment of the present invention, short coherence light source 110 is a superluminescent diode (SLD). Radiation 120 output from SLD 110 is collimated by lens system 130 into collimated beam 140. Collimated beam 140 impinges upon beam splitter 150 and is split into beams 160 and 170.

As further shown in FIG. 1, beams 160 and 170 output from beam splitter 150 impinge upon retroreflectors 180 and 190, for example mirrors 180 and 190, respectively. As should be well understood by those of ordinary skill in the art, SLD 110, lens system 130, beam splitter 150, and retroreflectors 180 and 190 are familiarly known in the art as a Michelson interferometer ("Michelson interferometer 187"). In accordance with the present invention, the difference d between the optical path length of radiation traversing arms 200 and 210 of Michelson interferometer 187 is chosen so that d=nl, where n is the index of refraction of a reference or standard human eye and l is the length of a reference or standard human eye. The index of refraction and length of a typical human eye is well known to those of ordinary skill in the art. For example, the index of refraction may be taken as 1.336 and the length l may be taken as 24 mm.

The reflected beams are combined by beam splitter 150 and impinge upon beam splitter 220. Beam splitter 220 directs a portion of the incident radiation towards lens 230 of eye 240. Eye lens 230 more or less focuses the incident radiation onto fundus 250 of eye 240, thereby generating a secondary light source on the fundus. Radiation emanating from this secondary light source on fundus 250 is collimated by eye lens 230 into substantially parallel beams in the case of an emmetropic eye, radiation output from an emmetropic eye is indicated by a continuous line. The collimated radiation passes through beam splitter 220 and impinges upon a relay lens system which includes relay lens systems 270 and 280. Radiation 290 output from relay lens system 260 impinges upon grating 300 and radiation output from grating 300 impinges upon diaphragm 305. Diaphragm 305 is comprised of at least three decentered apertures which are axially displaced from the optical axis of the relay lens system, FIG. 1 shows only two of the apertures, apertures 310 and 320 for ease of understanding the present invention.

Radiation impinging upon grating 300 is split into a first order bundle of radiation and a zero$^{th}$ order bundle of radiation. In accordance with methods which are well known to those of ordinary skill in the art, grating 300 is blazed so the first order bundle of radiation contains most of the diffracted radiation. Next, the radiation in the first order bundles, represented by continuous lines 360 and 370, is focused by focusing lens systems 380 and 390, respectively, as continuous lines 387 and 397, respectively, onto CCD linear detectors 400 and 410, respectively. Finally, output from CCD linear detectors 400 and 410 are provided as input to computer 500.

The following provides a description of how embodiment 100 is used: (a) to measure the refractive error of an eye and (b) to measure the length of the eye.

Measurement of the Refractive Error of an Eye

In the case of an emmetropic eye, radiation emanating from eye lens 230, as indicated by continuous lines 425 and 435, is comprised of beams which are substantially parallel. However, in the case of an ametropic eye, radiation emanating from eye lens 230, as indicated by dotted lines 420 and 430, is comprised of beams which are not parallel. As shown in FIG. 1, dotted lines 385 and 395 represent radiation impinging upon CCD linear detectors 400 and 410, respectively, which emanate from an ametropic eye and continuous lines 387 and 397 represent radiation impinging upon CCD linear detectors 400 and 410, respectively, which emanate from an emmetropic eye. Note that the radiation impinging upon CCD linear detectors 400 and 410, respectively, which emanated from an ametropic eye is laterally displaced from, and parallel to, the radiation impinging upon CCD linear detectors 400 and 410, respectively which emanated from an emmetropic eye. Further, in accordance with the present invention, the above-identified lateral displacement of the radiation on the respective CCD linear detector is proportional to the angle between dotted lines 420 and 430 (representing radiation emanating from an ametropic eye) and continuous lines 425 and 435, respectively, (representing radiation emanating from an ametropic eye) at eye lens 230. This angle is referred to below as the divergence angle.

Although not shown in FIG. 1, as is well known to those of ordinary skill in the art, grating 300 causes angular spreading of the first order radiation due to dispersion and this angular dispersion leads to a lateral spreading of the focus of the spot on the CCD linear detectors. As is also well known to those of ordinary skill in the art, CCD linear detectors 400 and 410 provide (as output to computer 500) a data vector representing the intensity distribution of radiation impinging thereon as a function of pixel number.

In accordance with the present invention, the envelope finction of the intensity distribution is a Gaussian distribution function which is modulated by Muller fringes; the formation of Muller fringes will be explained in more detail below in conjunction with a description of how embodiment 100 is used to measure the length of eye 240. In accordance with the present invention, the data vector output from each of CCD linear detectors 400 and 410 is correlated in computer 500 in a manner which is well known to those of ordinary skill in the art with a Gaussian template function stored in computer 500 (for example, in memory) using any one of a number of correlation techniques which are well known to those of ordinary skill in the art. Next, the position corresponding to the template function which provides the closest correlation with the data vector is stored in computer 500 (for example, in a memory device or in storage such as a disk) as the position coordinate of the spot of radiation on the respective CCD linear detector. A relationship between the divergence angle θ and the position coordinate of the spot of radiation on each of the CCD linear detectors for a particular embodiment of the present invention is determined in accordance with the following calibration procedure.

In accordance with the calibration procedure, a "fake" eye is formed, which fake eye is comprised of a lens that focuses incident radiation from SLD 110 onto a scattering target, for example, a paper, placed at the position of fundus 250. Next, the position of the spot on the respective CCD linear detectors is determined as a finction of position x of the scattering target. Position x=0 is the position where the radiation is focused on the scattering target (this emulates an emmetropic eye) and positions x≠0 are positions where the radiation is defocused on the scattering target (this emulates an ametropic eye). Next, the position of the spot on the respective CCD linear detectors is stored as a function of the position x. Lastly, the divergence angle θ is determined by using the fact that the measured displacement x of the scattering target is related to the divergence angle θ by the formula θ=x/f where f is the focal length of the "fake" eye.

The above-described information is then used in accordance with an analysis described in an article entitled "Sensors in Ophthalmology" by T. Hellmuth which appears at pp. 290–323 in a book entitled "Sensors Update," ed. by H. Baltes, W. Gopel, and J. Hesse, Published by Wiley-VCH Verlag GmbH, Weinheim, Germany in 1998 (the "Hellmuth article"). In particular, as described in the Hellmuth article, divergence angles in the x- and y-direction ($\theta_x$ and $\theta_y$) and the positions of two beams are sufficient to determine spherical and cylindrical refractive error of eye 240. The OPD (optical path deviation) of lens 230 of eye 240 can be expanded into three Zernike polynomials for defocussing and astigmatism as follows:

$$OPD(\rho, \phi) = \alpha Z_{sph}(\rho, \phi) = \beta Z_{cyl1}(\rho, \phi) + \gamma Z_{cyl2}(\rho, \phi) \tag{1}$$

where the "spherical" Zernike polynomial is defined as:

$$Z_{sph}(\rho, \phi) = 2\rho^2 - 1 \tag{2}$$

where the two "cylindrical" Zernike polynomials are defined as:

$$Z_{cyl1}(\rho, \phi) = \rho^2 \cos(2\phi) \tag{3}$$

$$Z_{cyl2}(\rho,\phi) = \rho^2 \sin(2\phi) \tag{4}$$

and where $(\rho,\phi)$ are polar coordinates of the beams at the pupil of eye 240.

The angles of the beams at the pupil of eye 240 are equal to the orientation of the gradient of the OPD. Thus, knowing the angles $\theta_{xi}$ and $\theta_{yi}$ of two beams at two points at the pupil with known coordinates $\rho_i$, $\phi_i$ (i=1, 2), the expansion coefficients α, β, γ can be calculated by solving the following linear equation system (i=1, 2):

$$\nabla_x OPD(\rho_i, \phi_i)/|\nabla OPD(\rho_i, \phi_i) = \cos(\theta_{xi}) \tag{5}$$

$$\nabla_y OPD(\rho_i, \phi_i)/|\nabla OPD(\rho_i, \phi_i) = \cos(\theta_{yi}) \tag{6}$$

The expansion coefficients α, β, γ are then used to describe the spherical refractive error (S), the cylindrical refractive error (C), and the angular orientation of the cylindrical refractive error Φ of eye 240 as follows.

$$C = (\beta^2 + \gamma^2)^{1/2} \tag{7}$$

$$\Phi = \tfrac{1}{2}\text{arctab}(\gamma/\beta) - 45° \tag{8}$$

$$S = \alpha - C/2 \tag{9}$$

In order to determine $\rho_i$, $\phi_i$ (i=1, 2), the known coordinates of the two beams at the pupil of eye 240, one uses the fact that $\rho_i$, $\phi_i$ are the polar coordinates of the image of the decentered apertures of diaphragm 305 (for example apertures 310 and 320 of diaphragm 305) at the pupil of eye 240. In the embodiment of the present invention shown in FIG. 1, the magnification is 1, therefore, $\rho_i$, $\phi_1$ are equal to the coordinates of the respective apertures. In particular, $\rho_i$ is the radial distance of the center of an aperture from the optical axis, for example, the optical axis of relay lens systems 270 and 280 and $\phi_i$ is the azimuthal angle relative to, for example, a vertical axis.

In an alternative embodiment of the present invention, compensating optics can be placed, for example, between eye 240 and relay lens system 270 to compensate for the refractive error of eye 240. Suitable compensating optics are described, for example, in U.S. Pat. No. 3,822,932 and in U.S. Pat. No. 4,650,301. In this case, the embodiment of the present invention becomes a "nulling device." Here, the compensating optics is adjusted until the displacement of, for example, beams 385 and 395 at CCD arrays 400 and 410, respectively, are zero. In a preferred embodiment, the adjustment is done automatically under the direction of computer 500.

Measurement of the Length of an Eye

In accordance with the present invention, and as described in the Fercher article with reference to FIG. 6 thereof, embodiment 100 comprises a dual-beam Michael interferometer. As disclosed in the Fercher article, the dual-beam interferometer is advantageous in that translational movement of eye 240 has no impact on the matching condition and does not generate an error in the distance measurement.

In accordance with the present invention, radiation (directed by beam splitter 220 towards eye 240 that is) reflected by findus 250 is superimposed with radiation (directed by beam splitter 220 towards eye 240 that is) reflected by cornea 235. If the distance between the light emitting sites, i.e., fundus 250 and cornea 235, is matched to the optical path difference d of Michelson interferometer 187, interferences between corresponding beam components will occur. In accordance with the present invention, the coherence function of the radiation field exiting the above-described dual-beam interferometer can be measured without moving parts using a spectrometer to provide a spectrum of the radiation source structured with Muller fringes. Further, in accordance with the present invention, the density of the Muller fringes is proportional to the mismatch between the true eye length and the standard eye length, l.

As described in the Fercher article, see in particular FIG. 17 and the discussion relating thereto, spectrometers in embodiment 100 shown in FIG. 1 are comprised of grating 300 and respective focusing lens systems 380 and 390, and respective CCD linear detectors 400 and 410.

The theory of operation of embodiment 100 can be understood as follows.

If one were to think of SLD 110 as a tunable monochromatic source, for sake of illustration, for a certain wavelength Michelson interferometer 187 would show no intensity at its output because of destructive interference. This is because Michelson interferometer 187 acts like a cavity with resonances. The free spectral range is $\delta v=c/(2bd)$ where d is the optical path length difference of radiation traversing the two arms of Michelson interferometer 187. If one uses SLD 110 with its broad spectrum as input to Michelson interferometer 187, the spectrum of the output of Michelson interferometer 187 shows "black" lines known as Muller fringes. However, the density of the lines in the output from Michelson interferometer 187 by itself is very high.

Eye 240 itself comprises a Fabry-Perot interferometer with an armlength difference 2nl providing Muller fringes with a density comparable to that of external Michelson interferometer 187. The free spectral range of the "eye interferomete" is $\delta v=c/(4nl)$. Muller fringes are also produced in this case at a density which is so high that they cannot be resolved by grating 300. However, in accordance with the present invention, if the eye arm length difference 2nl is close to d, the optical path length difference of radiation traversing the two arms of Michelson interferometer 187, this dual interferometer (the combination of Michelson interferometer 187 and eye 240) has resonances with a free spectral range of $\delta v=c/(2(d-2nl))$ which can be resolved by the grating spectrometers of embodiment 100.

In particular, this can be further understood as follows. Each wavelength component of the radiation output from SLD 110 is split by beam splitter 150 into partial beam a which travels in arm 200 (the short arm of Michelson interferometer 187) and partial beam b which travels in arm 210 (the long arm of Michelson interferometer 187). The optical path difference between arm 200 and arm 210 is d. Then, partial beam a is split into beam a1 and beam a2 by cornea 235 of eye 240. Beam a1 is reflected by fundus 250 and beam a2 is reflected by cornea 235. The optical path difference between beams a1 and a2 is 2nl. Partial beam b is also split at cornea 235 into partial beams b1 and b2. The four partial beams a1, a2, b1 and b2 are superimposed at the detector and interference terms are possible for all possible combinations. However, only superposition of partial beams a1 and b2 provides interference maxima as a function of wavelength which are separated well enough to be resolved by the grating spectrometers of embodiment 100. The separation between maxima is given by $\delta\lambda=\delta v\lambda^2/c=\lambda^2/(2(d-2nl))$. The necessary resolution of the spectrometer is $\delta\lambda/\lambda=\lambda/(2(d-2nl))$. With a grating of N=100 lines within the aperture of, for example, 1 mm, a resolution $\delta\lambda/\lambda=1/N=0.01$ is achievable. In this case, d−2nl<$N\lambda/2$=50 $\mu$m is the capture range of the eye length portion of embodiment 100. This is also in the order of the spectral width of SLD 110. The eye length variation of human eyes is much higher than 50 $\mu$m. It may be several millimeters. In order to cover this variation range, retroreflector 190 is mounted on a movable stage (not shown). The movable stage is translated by a stepper motor (not shown) with an accuracy better than the capture range of embodiment 100 determined by the resolution of the spectrometer and the coherence length of SLD 110. The stepper motor is controlled by computer 500 in a manner which is well known to those of ordinary skill in the art. In accordance with the present invention, the movable stage is translated until the Muller fringes are detected on the fringe detectors, i.e., CCD linear detectors 400 and 410. The position of the movable stage determines the arm length difference d.

The Muller fringes provide a modulation of the radiation intensity distribution on CCD linear detectors 400 and 410. To obtain the density of the Muller fringes, a piecewise Fourier transform of the CCD data output vector is performed in computer 500 in accordance with methods well known to those of ordinary skill in the art. This produces the local spatial modulation frequency which is used to determine the difference d−2nl, and from this, the length of eye 240.

As one of ordinary skill in the art readily appreciate from the above, advantageously, in accordance with the present invention, grating 300 is used for deflecting radiation to CCD linear detectors 400 and 410 to provide information relating to ametropia and for spectrum analyzing Muller fringes to provide information relating to the difference between the true length of eye 240 and l, the length of a standard eye.

Lastly, although the present invention has been described in terms of CCD linear detectors, those of ordinary skill in the art will readily appreciate that one can also use differential diodes. Differential diodes are comprised of two diodes separated by a narrow bar with a width in the order of 10 microns. When a beam of radiation having a diameter much larger than the bar width impinges upon the diodes symmetrically, both diodes generate the same photocurrent. However, when the beam of radiation is laterally displaced, the difference between the photocurrents of the two diodes is not equal to zero and, instead, is proportional to the displacement of the beam of radiation. A quadrant diode comprises four diodes separated by a cross having a bar width also in the order of 10 microns. It is well known to those of ordinary skill in the art that one can subtract and add photocurrents produced by the four diodes in predetermined ways to provide two signals which are proportional to the x and y displacements of the beam of radiation.

Those skilled in the art will recognize that the foregoing description has been presented for the sake of illustration and description only. As such, it is not intended to be exhaustive or to limit the invention to the precise form disclosed.

What is claimed is:

1. Apparatus which measures length and refractive error of an eye which comprises:
    a source of short coherence radiation which couples radiation into a Michelson interferometer having arms, the arms of the Michelson interferometer having a predetermined optical pathlength difference;
    an injector which couples radiation output from the interferometer into the eye;
    a relay system which couples radiation output from the eye to a spectrometer;
    wherein the spectrometer measures displacement of radiation to measure the refractive error and the spectrometer measures density of fringes to measure the length.

2. The apparatus of claim 1 wherein the predetermined optical pathlength difference is substantially equal to the product of a predetermined index of refraction and a predetermined length.

3. The apparatus of claim 2 wherein the spectrometer comprises a computer and a fringe detector and the computer measures the density of fringes output from the fringe detector.

4. The apparatus of claim 3 wherein the computer measures the density of fringes by piecewise Fourier transforming output from the fringe detector.

5. The apparatus of claim 4 wherein the fringe detector comprises a CCD detector.

6. The apparatus of claim 1 wherein the spectrometer comprises a grating, a transfer lens, and a fringe detector.

7. The apparatus of claim 6 wherein the spectrometer comprises a computer coupled to the output from the fringe detector.

8. The apparatus of claim 7 wherein the computer analyzes output from the fringe detector to determine displacement of radiation from a predetermined location.

9. The apparatus of claim 8 wherein the computer analyzes output from a predetermined number of fringe detectors to measure the refractive error.

10. The apparatus of claim 9 wherein the fringe detectors are CCD detectors.

11. Apparatus which measures length and refractive error of an eye which comprises:
    a source of short coherence radiation which couples radiation into a Michelson interferometer, the arms of the Michelson interferometer having a predetermined optical pathlength difference;
    an injector which couples radiation output from the interferometer into the eye;
    a refractive error correction apparatus;
    a relay system which couples radiation output from the eye to a spectrometer; and
    a computer coupled to the spectrometer and to the refractive error correction apparatus;
    wherein the computer interacts with the refractive error correction apparatus to counteract displacement of radiation indicated by output from the spectrometer to measure the refractive error and the computer measures density of fringes indicated by the output from the spectrometer to measure the length.

12. A method for measuring length and refractive error of an eye which comprises the steps of:
    coupling short coherence radiation into a Michelson interferometer having arms, the arms of the Michelson interferometer having a predetermined optical pathlength difference;
    coupling radiation output from the interferometer into the eye;
    coupling radiation output from the eye to a spectrometer;
    analying output from the spectrometer to measure displacement of radiation to determine the refractive error; and
    analyzing the output from the spectrometer to measure density of fringes to measure the length.

* * * * *